United States Patent
Thyr et al.

(10) Patent No.: US 10,625,190 B2
(45) Date of Patent: Apr. 21, 2020

(54) STEAM SEPARATION UNIT FOR A SYSTEM FOR HYDROLYSIS OF LIGNOCELLULOSIC BIOMASS MATERIAL

(71) Applicant: VALMET AB, Sundsvall (SE)

(72) Inventors: Anders Thyr, Sundsvall (SE); Örjan Ahlgren, Sundsvall (SE); Krister Sjöblom, Sundsvall (SE)

(73) Assignee: VALMET AB, Sundsvall (SE)

( * ) Notice: Subject to any disclaimer, the term of this patent is extended or adjusted under 35 U.S.C. 154(b) by 359 days.

(21) Appl. No.: 15/321,613

(22) PCT Filed: Jun. 24, 2015

(86) PCT No.: PCT/SE2015/050732
§ 371 (c)(1),
(2) Date: Dec. 22, 2016

(87) PCT Pub. No.: WO2015/199605
PCT Pub. Date: Dec. 30, 2015

(65) Prior Publication Data
US 2017/0157546 A1    Jun. 8, 2017

(30) Foreign Application Priority Data

Jun. 26, 2014 (SE) .................................. 1450788

(51) Int. Cl.
*B01D 45/12* (2006.01)
*B04C 5/18* (2006.01)
(Continued)

(52) U.S. Cl.
CPC ......... *B01D 45/12* (2013.01); *B01D 19/0063* (2013.01); *B01D 19/0068* (2013.01);
(Continued)

(58) Field of Classification Search
CPC ........ D21C 1/02; D21C 11/0007; D21C 7/12; D21C 7/06; D21C 1/00; D21C 9/02;
(Continued)

(56) References Cited

U.S. PATENT DOCUMENTS 2,086,701 A * 7/1937 Dreyfus ................... C13K 1/02
                                                                                    127/1
2,108,567 A * 2/1938 Scholler ................... C13K 1/02
                                                                                    127/1
(Continued)

FOREIGN PATENT DOCUMENTS

AU        7763681 A     5/1983
CA       1 159 772 A    1/1984
(Continued)

OTHER PUBLICATIONS

Indian Office Action for Indian Application No. 201637041528, dated Oct. 23, 2019, with an English translation.

*Primary Examiner* — Joseph W Drodge
(74) *Attorney, Agent, or Firm* — Birch, Stewart, Kolasch & Birch, LLP

(57) ABSTRACT

A steam separation unit for separation of steam from lignocellulosic biomass material in a hydrolysis process includes a treatment vessel including a separation section and a biomass collection section. The separation section is arranged with at least one inlet for receiving at least partly hydrolyzed biomass material mixed with steam and at least one control outlet for discharging the steam from the vessel. A biomass collection section arranged to be filled at least partly with liquid during operation and coupled to the separation section to collect the biomass material after separation from steam, wherein the biomass collection section includes a mixing element for mixing the biomass material with liquid and at least one control valve for discharging biomass material mixed with liquid. A system (Continued)

for hydrolysis of lignocellulosic biomass material including such a separation unit is also presented.

12 Claims, 2 Drawing Sheets

(51) Int. Cl.
| | | |
|---|---|---|
| *C13K 1/02* | (2006.01) | |
| *B04C 5/22* | (2006.01) | |
| *B01D 45/02* | (2006.01) | |
| *B01J 8/08* | (2006.01) | |
| *B01D 19/00* | (2006.01) | |
| *C12M 1/00* | (2006.01) | |

(52) U.S. Cl.
CPC ................ *B01D 45/02* (2013.01); *B01J 8/08* (2013.01); *B04C 5/18* (2013.01); *B04C 5/22* (2013.01); *C13K 1/02* (2013.01); *C12M 45/20* (2013.01)

(58) Field of Classification Search
CPC .. D21C 9/18; C08H 8/00; Y02E 50/16; C12P 2201/00; C12P 7/08; C12P 7/10; C08B 1/00; C13K 1/02; C13K 1/04; C13K 1/06; C13K 1/08; B01J 3/03; B01J 3/04; B01J 4/001; B01J 4/007; B01J 4/008; B01J 2203/00; B01J 2203/06; B01J 2204/00; B01J 2204/002; B01J 2204/005; B01J 2219/00162; B01J 2219/00164; B01J 8/08; B01D 45/12; B01D 45/02; B01D 19/00; B01D 19/0042; B01D 19/0063; B01D 19/0068; B01D 19/0094; B04C 5/22; B04C 5/18; C12M 45/20
USPC ................ 127/1, 36, 37; 422/112, 129, 241; 536/56, 124, 127, 128; 95/241, 260, 264; 96/155, 156, 157, 204
See application file for complete search history.

(56) References Cited

U.S. PATENT DOCUMENTS

| | | | | |
|---|---|---|---|---|
| 2,739,086 | A | * | 3/1956 | Kenaga ...................... B01J 3/02 127/1 |
| 2,858,213 | A | * | 10/1958 | Durant ..................... D21C 3/24 162/17 |
| 3,523,911 | A | * | 8/1970 | Funk ........................ D21C 3/04 502/419 |
| 3,802,956 | A | * | 4/1974 | Backlund ................. D21C 1/00 162/19 |
| 4,023,982 | A | * | 5/1977 | Knauth ................ C13K 13/002 127/1 |
| 4,076,507 | A | | 2/1978 | Hauberg |
| 4,427,453 | A | * | 1/1984 | Reitter ..................... C13K 1/02 127/1 |
| 6,284,096 | B1 | | 9/2001 | Hartmann |
| 6,428,591 | B1 | | 8/2002 | Bouchillon et al. |
| 10,047,408 | B2 | * | 8/2018 | Thyr ....................... C12P 19/02 |
| 2005/0115408 | A1 | | 6/2005 | Kilgore |
| 2009/0221814 | A1 | | 9/2009 | Pschorn et al. |
| 2009/0301673 | A1 | * | 12/2009 | Snekkenes ............... D21C 1/02 162/49 |
| 2010/0069626 | A1 | * | 3/2010 | Kilambi ................... C08H 8/00 536/56 |
| 2010/0263814 | A1 | * | 10/2010 | Dottori .................... D21B 1/36 162/21 |
| 2011/0206571 | A1 | * | 8/2011 | Skinner ................. B01J 19/006 422/198 |
| 2012/0058544 | A1 | * | 3/2012 | Genta ....................... B08B 1/04 435/262 |

FOREIGN PATENT DOCUMENTS

| | | |
|---|---|---|
| CN | 102247938 A | 11/2011 |
| CN | 102482690 A | 5/2012 |
| CN | 103429311 A | 12/2013 |
| EP | 2 725 134 A1 | 4/2014 |
| SE | 512 845 C2 | 5/2000 |
| WO | WO 2010/151706 A1 | 12/2010 |
| WO | WO 2012/092613 A2 | 7/2012 |

\* cited by examiner

STEAM SEPARATION UNIT FOR A SYSTEM FOR HYDROLYSIS OF LIGNOCELLULOSIC BIOMASS MATERIAL

TECHNICAL FIELD

The present invention relates to a separation unit for a system for hydrolysis of lignocellulosic biomass material. For example, the separation unit according to the present invention may preferably be used in a high-temperature process for hydrolysis of lignocellulosic biomass material. The present invention also relates to a system for hydrolysis of lignocellulosic biomass material including a separation unit.

BACKGROUND OF THE INVENTION

Today, in systems for hydrolysis of biomass material such as lignocellulosic biomass material steam separation units, such as cyclones, are used to separate the steam from the biomass material, which may be, for example, residues from agricultural production, grasses, and residues from forest related production. After the steam separation stage, the biomass material is fed to subsequent processing stages, for example using a plug screw. The equipment downstream the steam separation unit may, for example, include a dilution stage, for example a dilution vessel or dilution screw, where the biomass material is diluted. Thus, the process is conducted in steps, which requires means for feeding the biomass material between the different steps.

In such processes and such equipment, it might also be difficult to provide a satisfactory pressure lock, this is especially pronounced when the biomass material lacks interior structure and has low network strength. If the pressure lock is too weak, there is a risk for so called blow-back, which, in turn, may entail damages on the equipment and process disturbances.

Hence, there is a need of improved equipment for steam separation for use in system for hydrolysis of lignocellulosic biomass material.

SUMMARY OF THE INVENTION

An object of the present invention is to provide improved equipment for separating steam from biomass in a system for hydrolysis of lignocellulosic biomass.

Another object of the present invention is to provide improved equipment for separating steam from biomass for use in a high-temperature process for hydrolysis of lignocellulosic biomass.

A further object of the present invention is to provide an improved separation unit capable of steam separation in combination with dilution of at least partly hydrolyzed biomass material.

Another object of the present invention is to provide improved equipment for separating steam from biomass and biomass dilution that are capable of providing a pressure lock for biomass material having low network strength.

In the context of the present invention, the term "plug screw feeder" relates to a feeder comprising a screw or similar rotating means and which is capable of feeding or transporting lignocellulosic material through the feeder at increased or maintained density and that creates an essentially gas- and fluid-tight plug of the lignocellulosic material towards the end of the feeder. For example, according to an embodiment of such a plug screw feeder, a cross-sectional area of the circular housing of the feeder and the screw diameter decreases in the feeding direction thereby so as to create a decreasing space between the screw and the housing and thus resulting in an essentially gas- and fluid-tight plug of the lignocellulosic material towards the end of the feeder. According to another embodiment of a plug screw feeder, the cross-sectional area of the circular housing of the feeder is constant while the screw diameter and screw axis increases in the feeding direction thereby creating a decreasing space between the screw and the housing and thus resulting in an essentially gas- and fluid-tight plug of the lignocellulosic material towards the end of the feeder. As the skilled person realizes, there are other embodiments of feeders that achieves this purpose and thus are included within the definition of the term "plug screw feeder".

Further, in the context of the present invention, the term "pressure lock" refers to a pressure proof barrier or lock allowing different pressures on respective sides of the barrier.

According to a first aspect of the present invention, there is provided a steam separation unit for separation of steam from lignocellulosic biomass material in a hydrolysis process comprising a vessel including a separation part or section and a biomass collection part or section. The separation section is arranged with at least one inlet for receiving at least partly hydrolyzed biomass material mixed with steam and at least one control outlet for discharging the steam from the vessel. The biomass collection section is filled at least partly with liquid during operation and arranged to collect the biomass material after separation from steam, wherein the biomass collection section includes a mixing element for mixing the biomass material with liquid and at least one control valve for discharging biomass material mixed with liquid.

Thus, the present invention is based on the idea of using biomass dilution liquid in a combined steam separation and dilution unit to obtain a pressure lock in the unit. In other words, the steam separation unit according to the present invention achieves a combined steam separation and dilution where the dilution liquid also serves as a pressure lock in the separation unit. The use of the dilution liquid also as a pressure lock entails that biomass material having different degrees of viscosity can be processed without risk for blow-back. The pressure lock function will be provided even for sticky (low network strength) material.

The system according to the present invention relates to a separation unit and a system for hydrolysis of lignocellulosic biomass material including, for example, wood-based raw materials such as wood chips, sawdust, chipped or hammer-milled forest residuals, agricultural residues such as bagasse, sugar cane straw, wheat straw, corn stover, corncobs, and oil palm fruit residuals (so-called empty fruit bunches). Other types of biomass material include grasses, reeds and energy canes.

According to embodiments of the present invention, at least one control valve is arranged to control a liquid level of the biomass collection section.

According to embodiments of the present invention, the biomass collection section comprises a liquid addition control valve for controlling the flow of the liquid.

According to embodiments of the present invention, the liquid addition control valve is arranged to control the liquid level of the biomass collection section.

According to embodiments of the present invention, the control outlet of the vessel for discharging the steam is a pressure control valve.

According to embodiments of the present invention, the at least one control valve and/or the liquid addition control valve is/are arranged to control the level of the liquid in the biomass collection section to obtain a pressure lock.

According to embodiments of the present invention, the vessel is vertically elongated and the inlet is arranged such that the biomass and steam enters the vessel tangentially at the top of the vessel.

According to embodiments of the present invention, the biomass collection section is arranged below the separation section such that biomass that travels downwards in the separation section falls into the biomass collection section.

According to embodiments of the present invention, the mixing element for mixing the biomass material with liquid is an agitator.

According to embodiments of the present invention, the separation section comprises a rotatable element arranged to remove biomass material from the walls of the separation section during rotation of the element.

According to embodiments of the present invention, the rotatable element is a rotatable scraper arranged to remove deposited biomass material on the walls of the vessel.

According to embodiment of the present invention, the separation section is arranged to allow the biomass mass material to fall freely downwards to the biomass collection section under influence of gravity.

According to a further aspect of the present invention, there is provided a system for a hydrolysis process comprising at least one reactor for at least partly hydrolyzing lignocellulosic biomass material, wherein the at least one reactor includes means for addition of steam. A steam separation unit according to the first aspect of the present invention is coupled to receive the at least partly hydrolyzed material from the at least one reactor.

Further advantageous embodiments of the device according to the present invention and further advantages with the present invention emerge from the detailed description of embodiments.

BRIEF DESCRIPTION OF THE DRAWINGS

The present invention will now be described, for exemplary purposes, in more detail by way of embodiments and with reference to the enclosed drawings, in which.

DETAILED DESCRIPTION OF PREFERRED EMBODIMENTS

Figure 2:
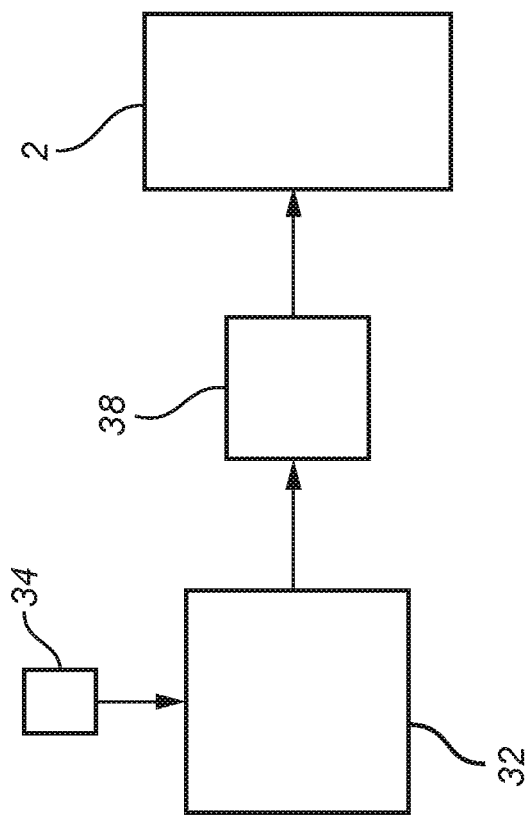
FIG. 2 is a schematic view of a system including a separation unit according to an embodiment of the present invention.

In the drawings, similar or corresponding elements are denoted by the same reference numbers.

For the purpose of this disclosure, the term longitudinal refers to the direction along which a body, part or element has its greatest extension. Further, when the term longitudinal is used in connection with the axes of screws, the longitudinal axis corresponds to the rotational axis of the screw.

Figure 1:
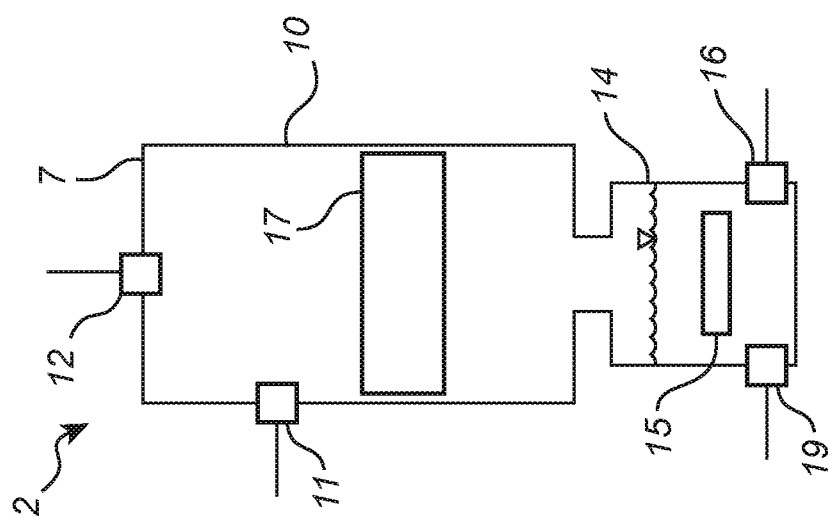
FIG. 1 is a schematic view of a separation unit according to an embodiment of the present invention.

With reference first to FIG. 1, the general principles of the separation unit according to the present system will be discussed. The separation unit according to the present invention may be used in a system for hydrolysis of biomass. The biomass material includes lignocellulosic biomass materials, for example, wood-based raw materials such as wood chips, sawdust, chipped or hammer-milled forest residuals, agricultural residues such as bagasse, sugar cane straw, wheat straw, corn stover, corncobs, and oil palm fruit residuals (so-called empty fruit bunches). Other types of biomass material include grasses, reeds and energy canes.

For example, the separation unit according to the present invention may preferably be used in a high-temperature process for hydrolysis of biomass such as residues from agricultural production, grasses, and residues from forest related production.

FIG. 1 schematically illustrates a separation unit 2 for separation of steam from biomass material in a hydrolysis process according to the present invention comprising a vessel 7 including a separation part or section 10 arranged with at least one inlet 11 for receiving biomass material mixed with steam and at least one control outlet 12 for discharging the steam. According to embodiments of the present invention, the separation section 10 is a pressure cyclone. The separation section 10 is vertically elongated and the inlet 11 is arranged such that the incoming stream of biomass and steam enters the separation section 10 tangentially at the top of the section 10. According to embodiments of the present invention, the incoming stream of biomass material and steam has an insoluble solids content of about 20-70%, and preferably 45-60%.

In embodiments of the present invention, the steam is vented upwards via a control valve 12, such as a pressure control valve. The biomass material moves downwards along the wall of the vessel 7. The pressure cyclone may operate at a pressure of 2-50 bar and at a temperature of 130-265° C.

The vessel 7 further comprises a biomass collection part or section 14 filled at least partly with liquid and arranged to collect the biomass material after the separation from steam. The biomass collection section 14 is arranged at a lower part of the treatment vessel 7 and preferably below the separation section 10 such that biomass that travels downwards in the separation section 10 falls into the biomass collection section 14. Thus, the separation section 10 is arranged to allow the biomass material to fall freely down to the collection section 14 under the influence of gravity.

The liquid level acts as a pressure lock between the vessel 7 with separation section 10 and the discharge, which enables pressurization of the vessel 7.

The biomass material that moves downward through the separation section 10 is collected in the biomass collection section 14. In embodiments of the present invention, the biomass collection section 14 is arranged in a funnel like shape or a tapering shape or similar to collect the biomass material that travels downwards in the separation section 10.

The biomass collection section 14 includes a mixing element 15 for mixing the biomass material with liquid and at least one control valve 16 for discharging biomass material mixed with liquid and controlling the liquid level. In the biomass collection section 14, the collected biomass material is mixed into the liquid. In embodiments of the present invention, an agitator 15 is used for mixing the biomass material into the liquid. In embodiments of the present invention, the stream of biomass material discharged from the biomass collection section has an insoluble solids content of about 5-20%.

The biomass collection section 14 is preferably always filled with liquid. According to embodiments of the present invention, the separation section 10 comprises a rotatable element 17 arranged to remove biomass material from the walls of the vessel during rotation of the element. For example, the rotatable element 17 is a rotatable scraper arranged to remove deposits (build-ups) of biomass material on the walls of the vessel. In embodiments of the present invention, the rotatable scraper is a rotating threaded element or rotating paddles.

According to embodiments of the present invention, the biomass collection section 14 comprises a liquid addition control valve 19 for controlling the flow of the liquid into the biomass collection section 14.

The at least one control valve 16 and/or the liquid addition control valve 19 can be used to control the level of the liquid in the biomass collection section 14 to obtain a pressure lock. The valves 16 and 19, together with the steam outlet control valve 12, co-operate to obtain an adjustable steam pressure within the steam separation section 10.

With reference now to FIG. 2, a system for a hydrolysis process including the steam separator according to the present invention will be discussed. At least one reactor 32 for at least partly hydrolyzing lignocellulosic biomass material including means 34 for addition of steam is arranged to at least partly hydrolyze the biomass material. For example, the at least one reactor 32 may be two reactors arranged in a two-stage hydrolysis process, as will be described below with reference to FIG. 3. A steam separation unit 2 according to the present invention and described above with reference to FIG. 1 is coupled to receive the at least partly hydrolyzed material from the at least one reactor 32. In this embodiment of a system, the at least one reactor 32 is coupled to the steam separation unit 2 via a second steam separator 38. In this embodiment, the pressure cyclone may operate at a pressure of 2-8 bar and at a temperature of 130-180° C.

Figure 3:
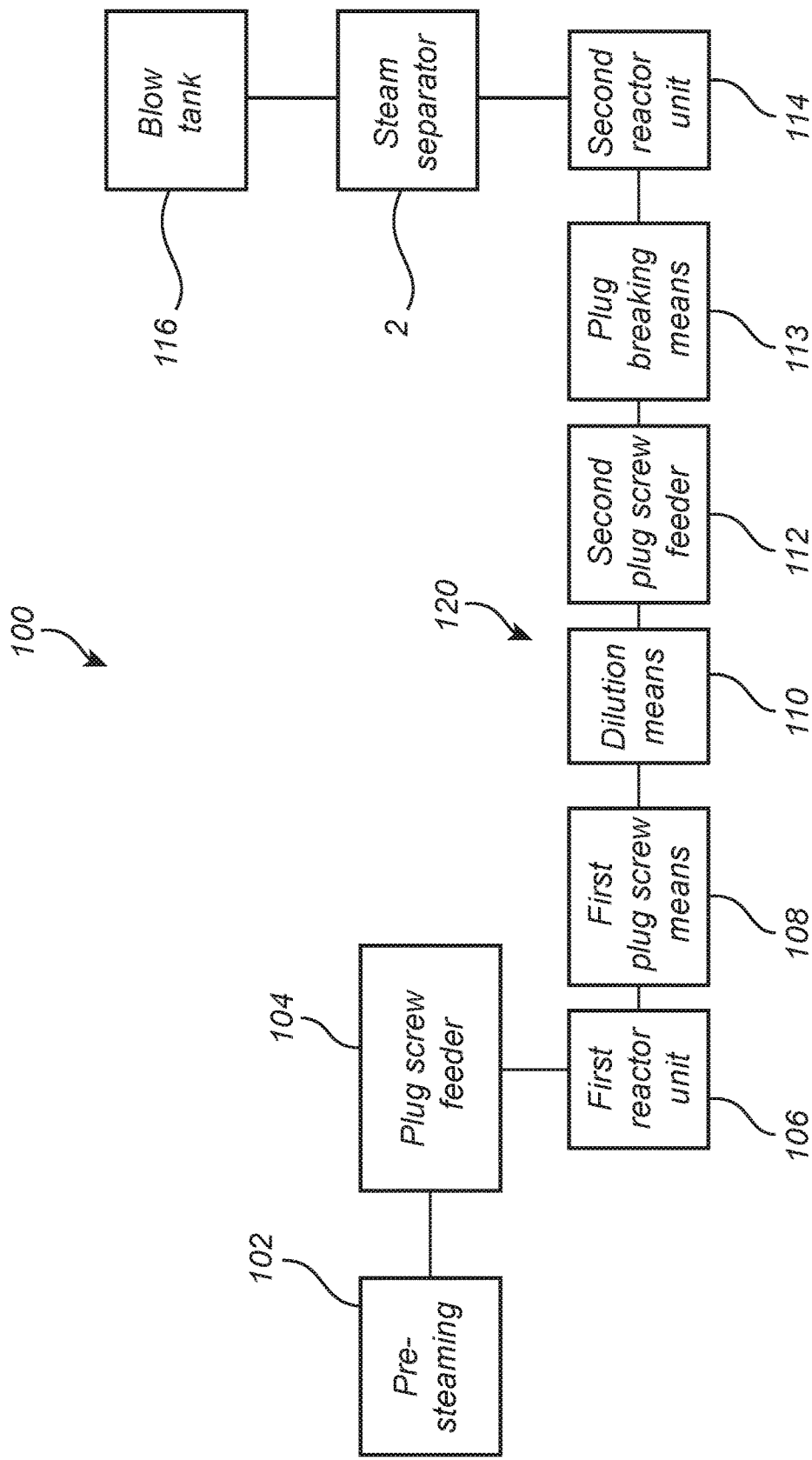
FIG. 3 is a schematic view of a system including a separation unit according to an embodiment of the present invention.

With reference now to FIG. 3, a system 100 for treatment of lignocellulosic biomass material in a hydrolysis process in which the present invention can be implemented will be described. In this exemplary system, a pre-steaming is the first stage and the final stage is a slurry of fully hydrolyzed biomass. Thus, the biomass material is received in the system in a pre-steaming stage 102. The pre-steaming vessel acts as a buffer for the biomass, providing, for example, a retention time of 10 minutes.

The second stage is a plug screw feeder 104. As the biomass is moved forward through the plug screw feeder 104, the biomass is compressed and dewatered. The compressed material forms a solid plug acting as a pressure seal.

The biomass material is then fed to a system for two stage hydrolysis according to the present invention, i.e. the biomass material is fed to a first reactor unit 106.

After the first reactor unit 106, the biomass material is fed further to an arrangement 120 for feeding and dewatering lignocellulosic material in a hydrolysis process between the first reactor unit 106, where the material is partly hydrolyzed, and a second reactor unit 114, where the partly hydrolyzed material is further hydrolyzed.

The first reactor unit 106 operates at a first pressure and the second reactor unit operates at a second pressure being higher than the first pressure.

Preferably, the first reactor unit 106 is arranged to operate in a temperature range between 140-220, preferably above 180° C. with a treatment time in a range between 1 second to 20 minutes, preferably below 5 minutes. Further, first reactor unit 10 is arranged to operate at a pressure within a range of 5-20 bar, preferably more than 10 bar, and more preferably within a range of 13-16 bar. The second reactor unit 114 is arranged to operate in a temperature range between 225-300, preferably above 235° C. with a treatment time in a range between 1 second and 10 minutes, preferably below 1 minute. Further, the second reactor unit 114 is arranged to operate at a pressure within a range of 25-50 bar, preferably at least 30 bar, and more preferably within a range of 35-45 bar.

The arrangement comprises a first plug screw feeder 108 arranged to receive the partly hydrolyzed material from the first reactor unit 106 and being arranged to compress, dewater and transport the material, wherein the first screw feeder is arranged to operate at a pressure of at least the first pressure.

Dilution means 110 is coupled to receive material from the first plug screw feeder 108 and includes a liquid inlet for receiving wash liquid, wherein the dilution means is arranged to maintain or increase the pressure.

A plug breaking means may be coupled between the first plug screw feeder 108 and the dilution means 110 to break up the plug and provide a pressure seal in case the plug is lost. It is also possible to add steam and/or acid to the biomass.

A second plug screw feeder 112 is arranged to receive the diluted material and is arranged to compress, dewater and transport the material to the second reactor unit 112, wherein the second screw feeder is arranged to operate at a pressure of at least the first pressure.

Preferably, the filtrate from both the first and the second plug screw feeder, 108 and 112, which is rich in hemicellulose sugars, is provided to a heat exchanger (not shown) before being collected for further processing.

A plug breaking means 113 may be coupled between the second plug screw feeder 112 and the second reactor unit 114 to break up the plug and provide a pressure seal in case the plug is lost. It is also possible to add steam and/or acid to the biomass in the dilution means 110.

After the second reactor unit 114, the processed biomass material is sent to a steam separator unit 2, for example, a steam separator according to the present invention. The steam separator unit 2 may be a cyclone where the steam and biomass material, or hydrolysis slurry, from the second reactor unit 114 enters the vessel tangentially along the wall. The biomass material falls along the wall towards the bottom and steam is separated by flashing and moves upwards. The pressure of the vessel is controlled with a control valve on the steam outlet. The separated material is discharged through the bottom via a blow valve. The steam may be recovered and used in the pre-steaming stage 102.

After dilution, the biomass material output from the steam separator 2 is collected in a blow tank 116 acting as a buffer between the reactor part of the process and the following separation and washing stages. The solid residual, which contains mainly lignin, can, for example, be sent to further refining or used to produce pellets.

The invention shall not be considered limited to the embodiments illustrated, but can be modified and altered in many ways by one skilled in the art, without departing from the scope of the appended claims.

The invention claimed is:

1. A steam separation unit for separation of steam from lignocellulosic biomass material in a hydrolysis process comprising:
   a vessel comprising:
      a separation section arranged with at least one inlet for receiving at least partly hydrolyzed biomass material mixed with steam and at least one control outlet for discharging the steam from the vessel; and
      a biomass collection section arranged to be filled at least partly with dilution liquid during operation and to collect the biomass material after separation from the steam, wherein the biomass collection section includes a mixing element for mixing the biomass material with dilution liquid, at least one control valve for discharging biomass material mixed with dilution liquid, and at least one liquid addition control valve, wherein the at least one control valve for discharging biomass material and the at least one liquid addition control valve control an amount of dilution liquid in the biomass collection section to provide a pressure lock, wherein different pressures occur on respective sides of said pressure lock, wherein the discharged biomass material from the biomass collection section has an insoluble solids content of about 5-20%, wherein the steam separation unit operates at a pressure of 2-50 bar and at a temperature of 130-265° C., and wherein the at least one control outlet of the vessel for discharging the steam, the at least one control valve for discharging biomass material and the at least one liquid addition control valve provide an adjustable steam pressure within the steam separation section.

2. The separation unit according to claim 1, wherein the at least one control outlet of the vessel for discharging the steam is a pressure control valve.

3. A system for a hydrolysis process comprising:
at least one reactor for at least partly hydrolyzing lignocellulosic biomass material, said at least one reactor including a steam generator for addition of steam; and
the steam separation unit according to claim 2 coupled to receive the at least partly hydrolyzed material from the at least one reactor.

4. The separation unit according to claim 1, wherein the vessel is vertically elongated and the at least one inlet is arranged such that the biomass and the steam enters the vessel tangentially at the top of the vessel.

5. The separation unit according to claim 1, wherein the biomass collection section is arranged below the separation section such that biomass that travels downwards in the separation section falls into the biomass collection section.

6. The separation unit according to claim 1, wherein the mixing element for mixing the biomass material with the dilution liquid is an agitator.

7. The separation unit according to claim 1, wherein the separation section comprises a rotatable element arranged to remove biomass material from walls of the separation section during rotation of the rotatable element.

8. The separation unit according to claim 7, wherein the rotatable element is a rotatable scraper arranged to remove deposited biomass material on the walls of the separation section.

9. The separation unit according to claim 8, wherein the rotatable scraper comprises a rotatable threaded element or a rotatable element including at least one paddle.

10. The separation unit according to claim 1, wherein the separation section is arranged to allow the biomass material to fall freely downwards to the biomass collection section under influence of gravity.

11. A system for a hydrolysis process comprising:
at least one reactor for at least partly hydrolyzing the lignocellulosic biomass material, said at least one reactor including a steam generator for addition of steam; and
the steam separation unit according to claim 1 coupled to receive the at least partly hydrolyzed material from the at least one reactor.

12. The system according to claim 11, wherein the at least one reactor is coupled to the steam separation unit via a second steam separation unit.

* * * * *